United States Patent
Burke et al.

(10) Patent No.: US 10,325,020 B2
(45) Date of Patent: Jun. 18, 2019

(54) CONTEXTUAL PHARMACOVIGILANCE SYSTEM

(71) Applicant: Accenture Global Solutions Limited, Dublin (IE)

(72) Inventors: Orlaith Burke, Dublin (IE); Md Faisal Zaman, Dublin (IE); John Vard, Dublin (IE); April Davis, Boston, MA (US); Nut Limsopatham, Dublin (IE)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 28 days.

(21) Appl. No.: 15/637,821

(22) Filed: Jun. 29, 2017

(65) Prior Publication Data

US 2019/0005019 A1    Jan. 3, 2019

(51) Int. Cl.
    *G06F 17/27*    (2006.01)
    *G06F 17/20*    (2006.01)
    *G06F 19/00*    (2018.01)

(52) U.S. Cl.
    CPC ........ *G06F 17/277* (2013.01); *G06F 17/2785* (2013.01); *G06F 19/36* (2013.01)

(58) Field of Classification Search
    CPC ........ G16H 10/60; G16H 50/20; G16H 10/20; G16H 50/70; G16H 70/20; G16H 50/30; G06F 19/324; G06F 19/00; G06F 19/24; G06F 17/2735; G06F 17/2755; G06F 17/2775; G06F 17/30625; G06F 17/30684; G06F 19/325; G06F 19/3456; G06Q 50/24; G06N 5/022; G06N 7/00; G06N 7/005
    See application file for complete search history.

(56) References Cited

U.S. PATENT DOCUMENTS

| 7,461,006 B2 * | 12/2008 | Gogolak | G06F 19/24 705/2 |
| 2002/0082868 A1 * | 6/2002 | Pories | G06F 19/324 705/3 |
| 2002/0165853 A1 * | 11/2002 | Gogolak | G06F 17/30595 |

(Continued)

OTHER PUBLICATIONS

Examination Report No. 1 issued in Australian Application 2018202580, dated Jun. 20, 2018, pp. 1-5, Australian Government, IP Australia, Phillip, Australia.

(Continued)

*Primary Examiner* — Michael Ortiz-Sanchez
(74) *Attorney, Agent, or Firm* — Brinks Gilson & Lione (57) ABSTRACT

Systems and methods for identifying an adverse effect of a pharmaceutical substance are provided. A system may tokenize an electronic medical record for a plurality of tokens. The system may further generate a distance score between a first vector of a word embedding model and a second vector of the word embedding model. The first vector may correspond to a substance token and the second vector may correspond to a condition token. The system may further detect an absence of a preventative association between the substance token and the condition token in a prevention repository. The system may further generate a causal link indication indicative of a causal link between the substance token and the condition token in response to the distance score being greater than a threshold value and detection of the absence of the preventative association between the substance token and the condition token.

17 Claims, 6 Drawing Sheets

(56) References Cited

U.S. PATENT DOCUMENTS

| | | | |
|---|---|---|---|
| 2007/0214009 A1* | 9/2007 | Epstein | G06Q 10/10 |
| | | | 705/2 |
| 2009/0099870 A1* | 4/2009 | Wilkinson | G06F 17/276 |
| | | | 705/3 |
| 2009/0119095 A1* | 5/2009 | Beggelman | G06F 19/00 |
| | | | 704/9 |
| 2010/0324927 A1* | 12/2010 | Tinsley | G06F 19/325 |
| | | | 705/2 |
| 2013/0041685 A1* | 2/2013 | Yegnanarayanan | G16H 50/20 |
| | | | 705/2 |
| 2013/0073554 A1* | 3/2013 | Bachert | G06F 19/324 |
| | | | 707/738 |
| 2013/0124523 A1* | 5/2013 | Rogers | G06F 19/32 |
| | | | 707/737 |
| 2014/0006013 A1* | 1/2014 | Markatou | G06F 17/3061 |
| | | | 704/9 |
| 2014/0046696 A1* | 2/2014 | Higgins | G06F 19/3456 |
| | | | 705/3 |
| 2014/0058744 A1 | 2/2014 | Nadarajah et al. | |
| 2015/0081323 A1 | 3/2015 | Jackson et al. | |
| 2016/0048655 A1 | 2/2016 | Maitra et al. | |
| 2017/0228500 A1* | 8/2017 | Massengale | G06F 19/322 |
| 2017/0293725 A1* | 10/2017 | Liu | G06F 19/321 |
| 2017/0329900 A1* | 11/2017 | Kato | C40B 30/02 |
| 2017/0351830 A1* | 12/2017 | Burger | G06F 19/00 |
| 2018/0082197 A1* | 3/2018 | Aravamudan | G06F 17/2785 |
| 2018/0089381 A1* | 3/2018 | Allen | G06N 5/022 |
| 2018/0089568 A1* | 3/2018 | Allen | G06N 5/022 |
| 2018/0101598 A1* | 4/2018 | Allen | G06F 17/2715 |

OTHER PUBLICATIONS

Alan R. Ronson et al., "An overview of MetaMap: historical perspective and recent advances", pp. 1-9, JAMIA, May 4, 2010.

Youngduck Choi et al., "Learning Low-Dimensional Representations of Medical Concepts", pp. 1-10, AMIA—Proceedings—AMIA Joint Summits on Translation Science, Jul. 20, 2016.

U.S. Appl. No. 14/826,575, filed Aug. 14, 2015, Maitra et al.

Examination Report No. 1, issued in Australian Application No. 2017210493, dated Oct. 4, 2018, pp. 1-6, IP Australia, Phillip, Australia.

Examination Report No. 4, issued in Australian Application No. 2015213399, dated Jul. 26, 2017, pp. 1-6, IP Australia, Phillip, Australia.

Extended European Search Report, issued in European Application No. 15181099.1, dated Jan. 19, 2016, pp. 1-10, European Patent Office, Munich, Germany.

European Office Action, issued in European Application No. 15181099.1, dated Dec. 20, 2016, pp. 1-13, European Patent Office, Munich, Germany.

Examination Report No. 1, issued in Australian Application No. 2015213399, dated Aug. 5, 2016, pp. 1-3, IP Australia, Phillip, Australia.

Examination Report No. 2, issued in Australian Application No. 2015213399, dated Jan. 11, 2017, pp. 1-4, IP Australia, Phillip, Australia.

Examination Report No. 3, issued in Australian Application No. 2015213399, pp. 1-4, dated May 24, 2017, IP Australia, Phillip, Australia.

* cited by examiner

CONTEXTUAL PHARMACOVIGILANCE SYSTEM

TECHNICAL FIELD

This disclosure relates to natural language processing and, in particular, to pharmacovigilance with natural language processing.

BACKGROUND

Substances, such as drugs, may cause symptoms in a patient other than to the intended/therapeutic goal. In some instances, the symptoms may be adverse. As pharmaceutical companies conduct research, perform clinical trials, comply with government reporting requirements, or generate other information related to a pharmaceutical substance, large quantities of pharmaceutical records may amass. In many circumstances, the pharmaceutical records may follow various formatting schemes, medical term conventions, and have other variations that result in inconsistencies between the records. It may become increasingly difficult to efficiently identify, classify, or otherwise interpret the adverse effects of pharmaceutical substances in a reasonable amount of time or with a reasonable amount of computing resources. Thus, present approaches to pharmacovigilance suffer from a variety of drawbacks, limitations, and disadvantages. There is a need for inventive systems, methods, components, and apparatuses described herein.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

DETAILED DESCRIPTION

By way of an introductory example, systems and methods to identify an adverse effect of a pharmaceutical substance are provided. For example, a system may include a medical term tokenizer. The medical term tokenizer may tokenize an electronic medical record for a plurality of tokens. The plurality of tokens may include a substance token corresponding to a pharmaceutical substance and a condition token corresponding to a medical condition.

The system may further include a semantic comparator. The semantic comparator may generate a distance score between a first vector of a word embedding model and a second vector of the word embedding model. The first vector may correspond to the substance token and the second vector may correspond to the condition token.

The system may further include a medical term contextualizer. The medical term contextualizer may detect an absence of a preventative association between the substance token and the condition token in a prevention repository. The prevention repository may link a first medical term identifier corresponding to the pharmaceutical substance with a second medical term identifier corresponding to the medical condition.

The system may further include a token validator. The token validator may generate a causal link indication indicative of a causal link between the substance token and the condition token in response to the distance score being greater than a threshold value and detection of the absence of the preventative association between the substance token and the condition token.

One interesting feature of the systems and methods described below may be that historical medical information stored in a word embedding model may provide context for determining a causal relationship between a pharmaceutical substance and a medical condition identified an electronic medical record. Alternatively, or in addition, an interesting feature of the systems and methods described below may be that medical terms that are incorrectly spelled or include alternative spellings may be correctly identified and analyzed based on the historical medical information stored in the word embedding model. Additional benefits, concepts, and design considerations are evident in the systems and methods described below.

Figure 1:
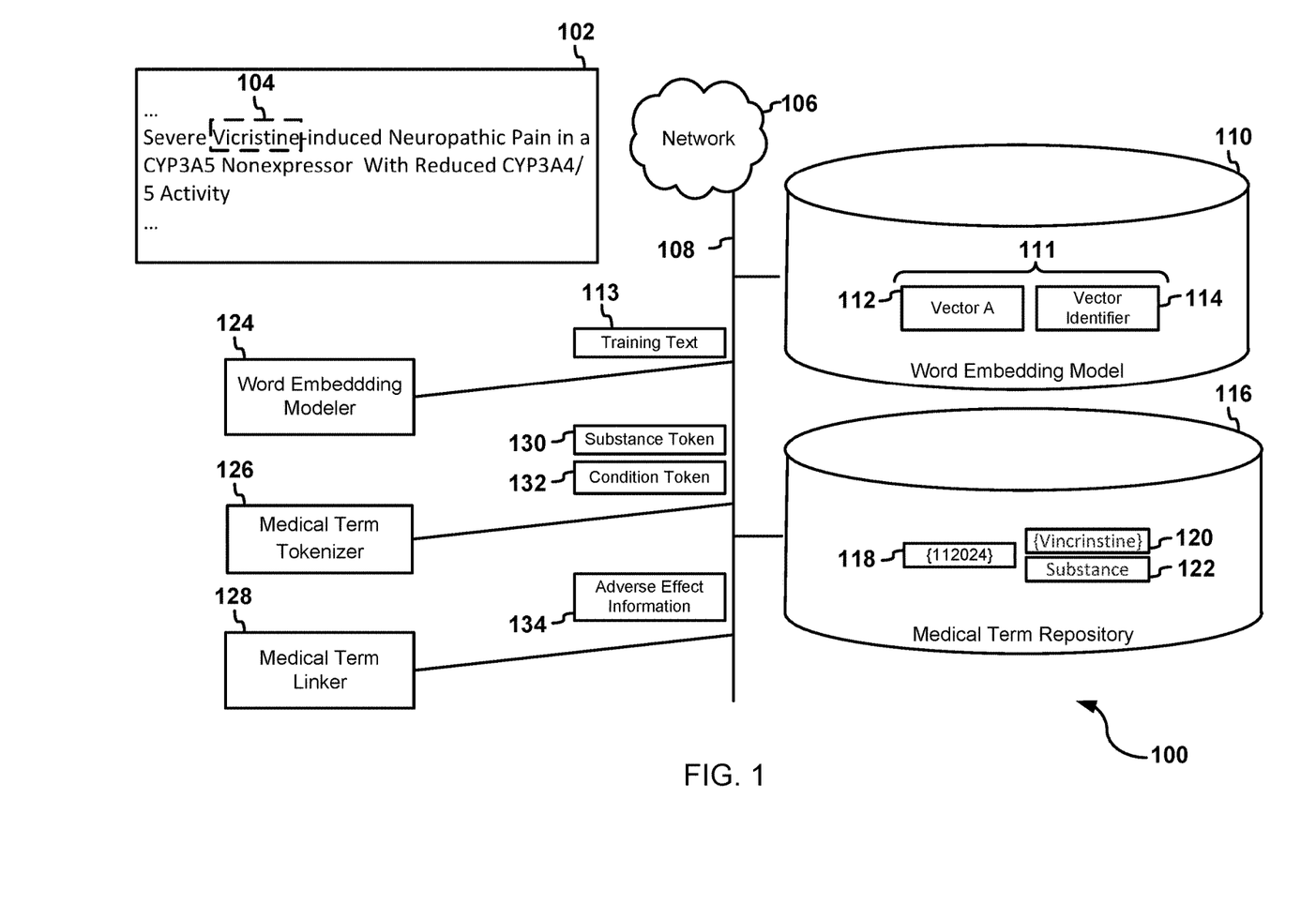
FIG. 1 illustrates an example of a system to identify an adverse effect of a pharmaceutical substance.

FIG. 1 illustrates an example of a system 100 to identify an adverse effect of a pharmaceutical substance. An electronic medical record 102 may include any electronic-based collection of medical information. The electronic medical record 102 may include text that describes pharmaceutical information. For example, the electronic medical record 102 may include a medical journal or a medical form. The electronic medical record 102 may include text and/or machine readable instructions, such as HTML. Alternatively or in addition, the electronic medical record may include medical information arranged in ASCII, Unicode, or any other computer character set.

The electronic medical record 102 may include a character segment 104. The character segment 104 may include any portion of the electronic medical record 102. The character segment 104 may include any form of character including one or more letter, symbol, number, and/or control character. The character segment 104 may include text and/or machine readable instructions, such as HTML. Alternatively or in addition, the character segment 104 may include medical information arranged in ASCII, Unicode, or any other computer character set. In addition, the character segment 104 may correspond to medical information related to a medical substance or a medical condition. The character segment 104 may include any group of characters, such as a word, symbol, sentence, or any group of information in the electronic medical record 102.

The system 100 may further include an information bus 108. The information bus 106 may include a network component, circuitry, a memory bus, or any other component that communicates electronic information. The information bus 106 may receive the electronic medical record 102. For example, the information bus 106 may receive the electronic medical record 102 communicated by a network 106. The network 108 may include, for example, a LAN, a WAN, or any other type of network configured to exchange information. In some examples, the network 108 may include a social media network or other type of network configured to exchange information between applications. In other examples, information bus 106 may receive the electronic medical record 102 may from a database. Alternatively or in addition, the information bus 106 may receive the electronic medical record from any network and/or memory accessible by the information bus.

The system 100 may further include a word embedding model 110. The word embedding model 110 may include any natural language processing model that represents text as vectors in a vector space. For example, the word embedding model 110 may include, for example, a continuous bag of words, skip-gram model, global vector (GloVe) model, FastText model, and/or any other type of vector-based model. In addition, the word embedding model 110 may include logic, mathematical formulas, and algorithms related to the word embedding model 110.

The word embedding model 110 may include word embeddings 111. The word embeddings 111 may include mappings between text and a mathematical representation of text. The word embeddings may be a result of a collective set of Natural Language Processing (NLP) techniques which involve, for example, mathematically mapping one word per dimension to a continuous embedding vector. In some examples, the word embeddings 11 may include a vector 112 and a vector identifier 114.

The vector 112 may mathematically represent the text in the word embedding model 110. In some examples, the vector 112 may be an embedding vector which represents the distributional semantics of a single word as real numbers. The semantics may be based on a corpus in which the word is contained. Alternatively or in addition, the vector 112 may be associated with a vector identifier 114 and represent text associated with or included in the vector identifier 114.

The vector identifier 114 may identify the text corresponding to the vector 112. The vector identifier 114 may include text. Alternatively or in addition, the vector identifier 114 may include an identifier, for example a primary or foreign key, associated with the text. The text associated with the vector identifier 114 and/or the vector 112 may include the training text 113, described below The system 100 may further include a medical term repository 116. The medical term repository 116 may include a repository that uniquely identifies medical terms or concepts. In some examples, the medical term repository 116 may include a database or a portion of a database. In other examples, the medical term repository 116 may include any data structure, for example, a dictionary that creates associations between medical terms and related information. For example, the medical term repository 116 may associate, among other information, a medical term identifier 118, a medical term label 120, and a medical term type 122.

The medical term identifier 118 may include an identifier of a medical term. In some examples, the medical term identifier 118 may include a primary or a foreign key in a database. In other example, the medical term identifier 118 may include numbers or text that are representations of the medical term.

The medical term label may include a preferred label of a medical term. For example, the medical term label 120 may include text that is the preferred spelling of the medical term. Alternatively, the medical term label 120 may include a primary key or a foreign key associated with the text that is the preferred spelling of the medical term.

The medical term type 122 may identify a type of medical concept the medical term identifier and/or label refer are associated with. For example, the medical term type may include a condition type and/or a substance type. The condition type indicate that the medical term identifier relates to a medical condition. The substance type may indicate that the medical term identifier relates to a pharmaceutical substance. In the example illustrated in FIG. 1, the medical term identifier 118 identified as "112024" a unique an identifier is associated with the medical term label 120 identified as "Vincristine". The medical term type 122 associated with the medical term identifier 118 illustrated in FIG. 1 is identified as "Substance". Accordingly, the medical term repository illustrated in FIG. 1 uniquely identifies "Vincristine" as a pharmaceutical substance. In other examples, the medical term identifier may include associations between one or more medical concept and one or more medical terms.

The system 100 may further include a word embedding modeler 124, a medical term tokenizer 126, and a medical term linker 128. The word embedding modeler 124 may manage the word embedding model 110. For example, the word embedding modeler 124 may receive the electronic medical record 102. The word embedding modeler 124 may create, read, update, and/or delete the word embeddings 111. For example, the word embedding modeler 124 may store the word embeddings 111 in the word embedding model 124. In some examples, the word embedding modeler 124 may train the word embedding model 110. For example, the word embedding modeler 124 may receive multiple electronic medical records and other medical-related information and update the word embedding model 110. As electronic medical records are received over time, the word embedding model may become increasingly sophisticated and capable of generating rich associations between vectors.

In some examples, the word embedding modeler 124 may train the word embedding model 110 with the training text 113. The training text 113 may include text from one or more medical document and/or electronic medical record. For example, the training text 113 may include a historical corpus of one or more medical record. Alternatively or in addition, the training text may include a new corpus of one or more medical record. Training the word embedding model 110 with historical medical information may create associations between vectors in the word embedding model 110. The vector identifier 114 may identify or include training text 113 provided to the word embedding model 110. The training text 113 may include text from historical medical documents and/or the electronic medical record 102. Accordingly, the vector 112 may correspond to the training text 113, or a portion thereof. In some examples, the word embedding model may store the training text 113.

With the expanding electronic medical records, word embedding modeler 124 will update the association between the word embeddings 111 on the new corpus (electronic medical records). In one example, to train the word embedding model 110 medical entities in each sentence in a medical record may be transformed into unique medical concept identifiers. Word embedding 111 may be generated for each of the unique medical concept identifiers based on a set of medical concept identifiers that are adjacent to that medical concept identifier in the collection of electronic medical records. The size of this set of adjacent medical concept identifiers are defined as a window. The positional information of the adjacent medical concept identifiers in the electronic medical record are used to find adjacent medical concept identifiers.

The medical term tokenizer 126 may tokenize the electronic medical record 102. By tokenizing the electronic medical record, the medical term tokenizer may identify portions of the electronic medical record 102 into meaningful elements called tokens. For example, the medical term tokenizer 126 may parse the electronic medical record 102 and identify medical terms in the electronic medical record 102. For example, the medical term tokenizer 126 may identify medical information included in the electronic medical record 102. For example, the medical term tokenizer 126 identify the medical term identifier 118 that is representative of the character segment 104 of the electronic medical record 102. Alternatively or in addition, the medical term tokenizer 126 may compare the character segment 104 with the medical term label 120 associated with the medical term identifier 118 to determine whether the medical term identifier 118 is representative of the character segment 104.

In some examples, the medical term tokenizer 126 may authenticate that the medical term identifier 118 is representative of the character segment 104 based on a comparison of the character segment 104 with the medical term label 120. The medical term label 120 may include text that is different from the character segment 104. For example, as illustrated in FIG. 1, the character segment 104 may include "Vicristine" and the medical label may include "Vincristine". The medical term tokenizer 126 may verify that the medical term label 120 and/or the medical term identifier 118 is representative of the character segment 104.

In some examples, the medical term tokenizer 126 may determine an alternative label for a medical term identifier 118. For example, the medical term tokenizer may determine that the training text included in the word embedding model 110 is an alternative representation of the character segment 104. In some examples, the medical term tokenizer 126 may evaluate the character segment 104 and a context of the character segment 104. The context of the segment may include text adjacent to the character segment 104. One or more vectors corresponding to the context may be associated with a target vector corresponding to the training text 113. The medical term tokenizer 126 may identify the target vector. The vector identifier 114 of the target vector may identify the training text 113. Medical term tokenizer 126 may communicate information indicative of the training text 113 representing the character segment 104.

In some examples, the medical term tokenizer 126 may determine a token corresponding to the character segment 104. A token may include information that indicates the character segment 104 is indicative of a medical term. For example, the token may include, the character segment 104, the medical term identifier 118, the medical term label 120, the medical term type 122, the training text 113, and/or other information that indicates the character segment 104 represents a medical term identified in the medical term repository 116, the word embedding model 110, or any other repository including medical terms and concepts. In some examples, the medical term tokenizer 126 may generate a substance token 130 and a condition token 132.

The substance token 130 may include an example of the token that relates the character segment 104 to a pharmaceutical substance. For example, the substance token 130 may include information that relates the character segment 104 to the medical term identifier 118 associated with the medical term type 122 that indicates a pharmaceutical substance. The condition token 132 may include an example of the token that relates the character segment 104 to a medical condition. For example, the condition token 132 may include information that relates the character segment 104 to the medical term identifier 118 associated with a medical term type 122 that is indicative of a medical condition.

The medical term linker 128 may identify an association between a medical condition and a pharmaceutical substance referred to by the electronic medical record 102. For example, the medical term linker may identify that the pharmaceutical substance corresponding to the substance token 130 causes, induces, or otherwise creates an adverse effect corresponding to the condition token 132. The medical term linker 128 may generate adverse effect information 134. The adverse effect information 134 may include information indicative of an association between the substance token 130 and the condition token 132. For example, the adverse effect information 134 may include identifying information related to the medical condition and/or the pharmaceutical substance, including, for example, the medical term identifier 118, the medical term label 120, the medical term type 122, the training text 113, and/or any other information stored in the medical term repository, the word embedding model 110, or any repository configured to store medical terms and concepts.

The electronic medical record 102 may identify medical terms or medical concepts that are misspelled or include alternative spellings that vary from a preferred spelling. Alternatively or in addition, the electronic medical record 102 may identify concepts related to medical terms. For example, the electronic medical record may include the text "Neuropathic" which relates the medical term "Neuralgia." The medical term tokenizer 126 may evaluate the character segment 104 to determine the medical term representing the character segment 104. Alternatively or in addition, the medical term tokenizer 126 may evaluate a context of the character segment 104 to increase the accuracy of identifying the medical term. For example, the medical term tokenizer 126 may identify alternative medical terms and/or alternative spellings of medical terms by evaluating the context of the segment with the word embedding model 110. As nomenclature of medical terms and concepts evolve over time, the word embedding modeler 124 may train the word embedding model 110 with the training text 113 that includes changes in medical nomenclature. Accordingly, the medical term tokenizer 126 may provide improved spell-checking, identification of alternative spelling, and authentication of medical term representations in the electronic medical record 102.

Figure 2:
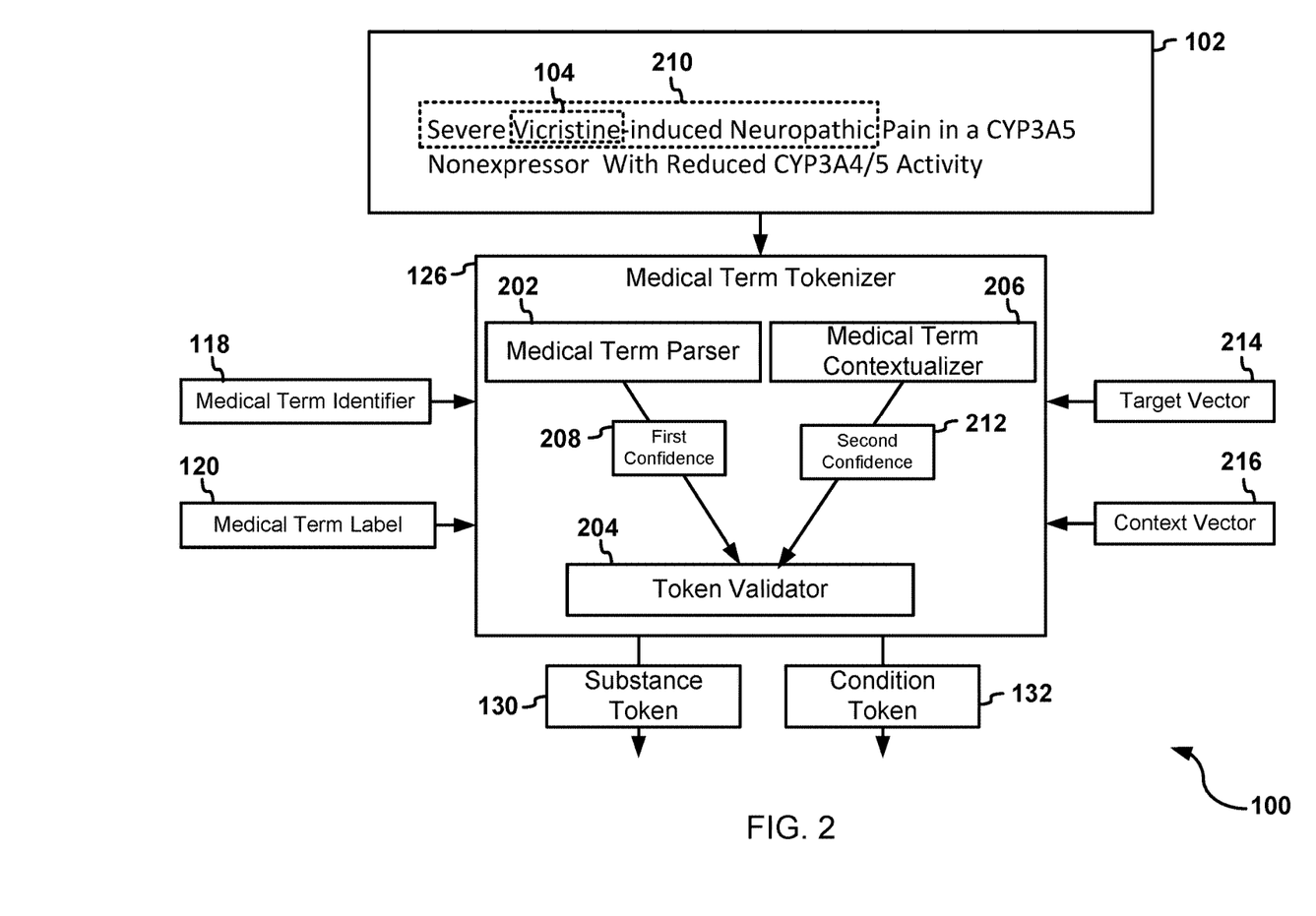
FIG. 2 illustrates an example of a medical term tokenizer.
Figure 3:
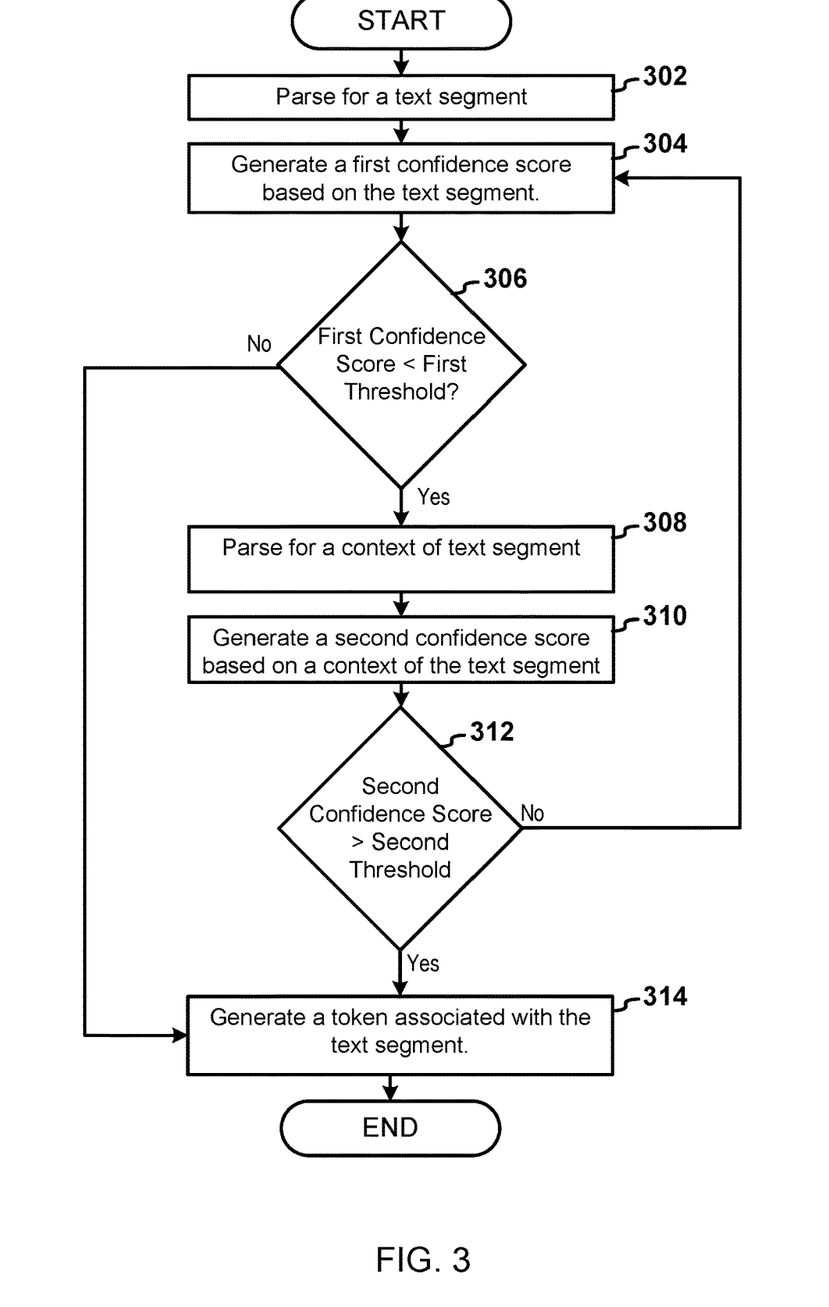
FIG. 3 illustrates an example of flow logic for a medical term tokenizer.

FIG. 2 illustrates an example of a medical term tokenizer 126. FIG. 3 illustrates an example of flow logic for the medical term tokenizer 126. References to FIG. 2 and FIG. 3 are included in the following discussion of the medical term tokenizer 126.

The medical term tokenizer 126 may include a medical term parser 202, a token validator 204 and a medical term contextualizer 206. The medical term parser 202 may parse the electronic medical record for the character segment 104 in the electronic medical record 102 (302). For example, the medical term parser 202 may parse the electronic medical for a word, pattern, symbol, groups of characters, or any other type of information grouping. In some examples, the medical term parser 202 may identify the character segment 104 by matching the character segment 104 with the medical term label 120 associated with the medical term identifier 118. In other examples, the character segment 104 may include a misspelled medical term or an alternative spelling of a medical term. The medical term parser 202 may perform analysis to determine whether the character segment 104 corresponds to the medical identifier.

The medical term parser 202 may generate a first confidence score 208 based on the character segment 104 (304). The first confidence score 208 may include a confidence that the medical term identifier 118 is representative of the character segment 104. For example, the first confidence score 208 may include an accuracy, probability, or any other statistical measurement that the character segment 104 is representative of the medical term identifier 118 or a medical term label 120. In some examples, the medical term parser 202 may determine the first confidence score 208 based on a comparison the character segment 104 with the medical term label 120. For example, the character segment 104 may include "vicristine", which is a misspelling of the medical term "vincristine". The first confidence score 208 may include a probability, an accuracy, or any other kind of statistical measurement, that the medical term label 120, "vincristine", is representative of the character segment 104, "vicristine".

To generate the first confidence score 208, the medical term parser 202 may utilize any type of spell checking or alternative word recognition algorithm. In some examples, the medical term parser 202 may combine one or more analysis for identifying misspelled medical terms. For example, the medical term parser 202 may determine misspelled terms and/or their alternative spellings based on whether the term and/or the alternative spelling is found in a medical dictionary. In some examples, if the medical term is found to be spelled incorrectly or if there are alternative version of the medical term, then candidate terms are generated based on string distance analysis, including, for example, a Levenshtein distance metric. The first confidence score may be based on the Levenshtein metric, or any other type of string metric. In some examples, the medical term parser 202 may adjust the first confidence score. For example, the medical term parser 202 may edit the medical term by replacing/adding characters and checking whether the edited term is found in the medical dictionary. If the term is found then the medical term parser may increase the first confidence score 208. If the term is not found, then the medical term parser may decrease the first confidence score 208.

The token validator 204 may determine the first confidence score 208 is greater a first threshold value (306). In response to the first confidence score 208 being greater than the first threshold value (306, No), the token validator 204 may generate a token, for example the substance token 130 and/or the condition token 132, associated with the character segment 104. The first confidence threshold may include a confidence threshold at which token validator may determine the character segment 104 corresponds, or does not correspond, to a medical term identifier 118. In response to the confidence value being less than then the first confidence threshold (306, Yes) the medical term contextualizer 206 may proceed to conduct additional contextual analysis of the character segment 104.

The medical term contextualizer 206 may parse the electronic medical record 102 for a context 210 of the character segment 104 (308). The context 210 of the character segment 104 may include contextual text. The contextual text may include any text adjacent to the character segment 104 or including the character segment 104. For example, the contextual text may include one or more portions of the electronic medical record 102 surrounding the character segment 104. In some examples, the context 210 may include the character segment 104. Alternatively, the context 210 may exclude the character segment 104. As illustrated in FIG. 2, the character segment 104 may include "Vicristine" and the context may include "Severe", "Vicristine", "Neuropathic", and/or "Pain". In other examples, the context may include additional or fewer portions of the electronic medical record 102.

The medical term contextualizer 206 may generate a second confidence score 212 based on the context 210 of the character segment (310). The second confidence score 212 may include a confidence of the training text 113 being associated with the context 210 in the word embedding model. Alternatively or in addition, the second confidence score may include an accuracy, a probability, or any other type of statistical measurement that the training text 113 from medical information used to train the word embedding model 110 is representative of the character segment 104.

In some examples, the second confidence 212 score may include, or be calculated based on, a distance measurement between vectors in the word embedding model 110. For example, the word embedding model may include a target vector 214 and a context vector 216. The target vector 214 may be associated with a first training text. The context vector 216 may be associated with a second training text. The second training text may include text from the context 210 of the character segment 104. Accordingly, the context vector 216 may be identified based on the context 210. Nearby vectors, including the target vector 214, may be associated with the context vector 216. The second confidence score 212 may include, or be calculated based on, the distance measurement between the target vector 214 and the context vector 216.

The distance measurement between vectors may include an angular distance between from between a vector and one or more additional vectors in the word embedding model 110. In some examples, the distance measurement may include, or be based on, a cosine similarity score and/or a cosine distance score.

The token validator 204 may determine whether the second confidence score 212 is greater than a second confidence threshold (312). In response to the second confidence score 212 being greater than a second threshold value, the token validator 204 may generate a token associated with the character segment 104 (314). In some examples, the token may include the substance token 130 and/or the condition token 132.

In response to the second confidence score 212 being less than the second threshold value (312, No), the token validator 204 my cause the medical term tokenizer to repeat the analysis using the training text 113 corresponding to the target vector 214 instead of the character segment 104. In some instances, the first confidence score 208 and/or the second confidence score may increase and the token validator 204 may generate token associated with the training text 113.

In other examples, the token validator 204 may determine a third confidence score that the training text is representative of a medical term. For example, the medical term parser 202 may compare the training text 113 to the medical term label 120. The third confidence score may include an accuracy that the training text 113 is a representation of the medical term identifier associated with the medical term label 120. In some examples, the token validator 204 may compare the third confidence score with the second confidence score 212. When the third confidence score decreases relative to the second confidence score 212, the token validator 204 may determine that the training text 113 is not representative of the medical term. Alternatively or in addition, the token validator 204 may compare the third confidence score with a threshold value to determine that the training text 113 is or is not, representative of the medical term.

The medical term tokenizer 126 may identify the substance token 130 and the condition token 132. The substance token 130 and the condition token 132 may be related based on an association indicated in the electronic medical record.

For example, the text "Vincristine-induced Neuropathic Pain" indicate a causal relationship between the text "Vincristine" and "Neuropathic". Natural language understanding of the electronic medical record may reveal a causal relationship between the substance token 130 and the condition token 132.

In some examples, it may be desirable to delay natural language understanding analysis due to the processing demand required by natural language understanding. Alternatively or in addition, it may be desirable to increase the accuracy of natural language understanding analysis. Accordingly, analysis of the electronic medical record 102, based on a pre-trained word embedding model and/or pre-populated medical information sources, may reveal a causal link between medical terms included in the electronic medical record 102.

Figure 4:
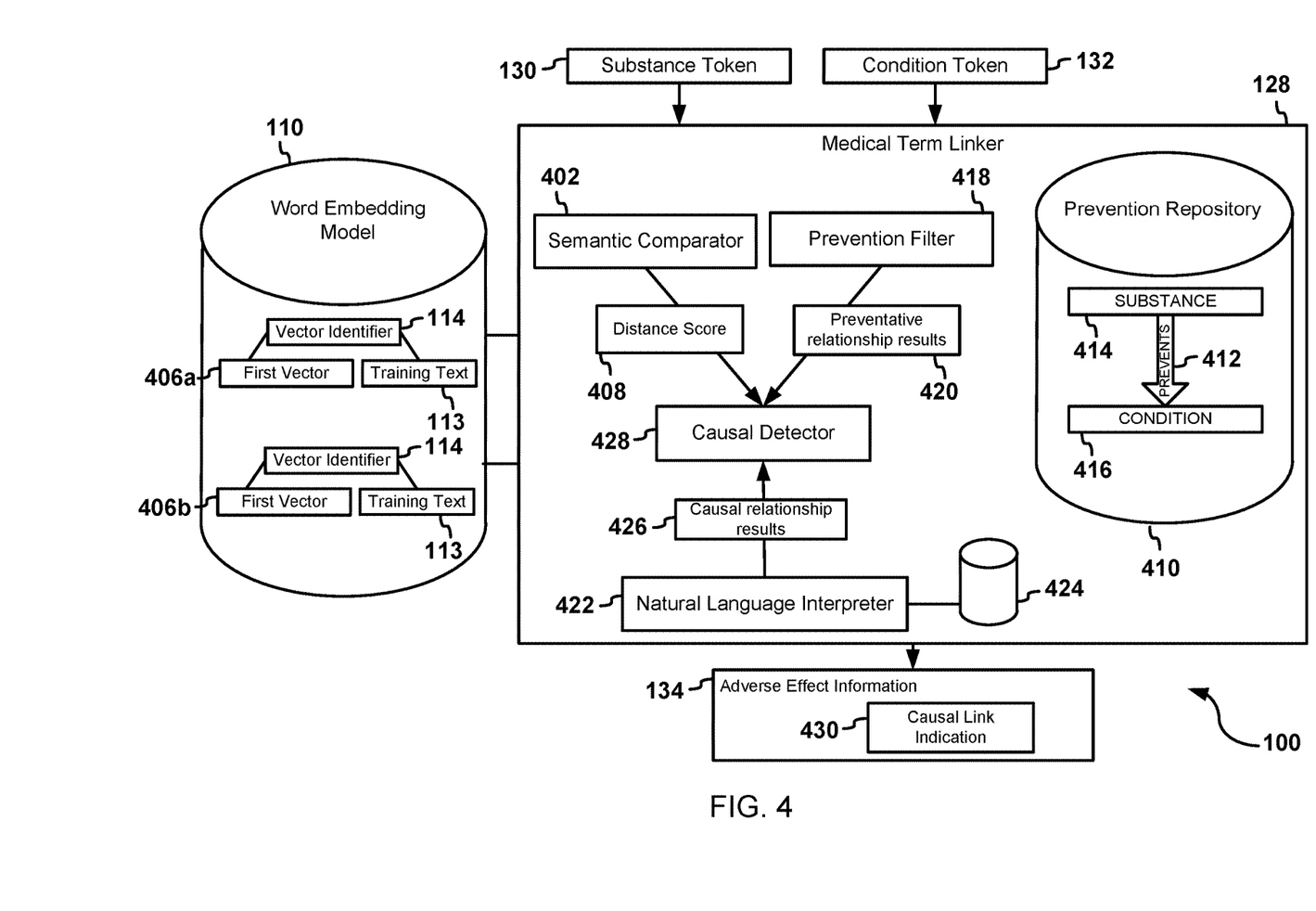
FIG. 4 illustrates an example of the medical term linker.

FIG. 4 illustrates an example of the medical term linker 128. The medical term linker 128 may include a semantic comparator. The semantic comparator 402 may identify one or more vectors 406 in the word embedding model 110 based on parameters provided to the semantic comparator. For example, the semantic comparator 402 may receive text and/or other identifiers and search the word embedding model 110 for the one or more vectors 406 corresponding to the text and/or identifiers. For example, the semantic comparator 402 may receive a token and compare the text of the token with the training text 113 associated with the vector in the word embedding model 110. The semantic comparator 402 may identify the vector based on a comparison of the text associated with the token with the training text 113 associated with the vector 112. In other examples, the semantic comparator 402 may compare the medical term identifier 118 with the vector identifier 114 to identify the vector 112.

The semantic comparator 402 may additionally calculate a distance score 408 between the vectors 406 in the word embedding model 110. For example, the vectors 406 may include a first vector 406a and a second vector 406b. The semantic comparator 402 may calculate a distance score 408 between the first vector 408a and the second vector 408b. The first vector 408a may, for example, correspond to the substance token 130 and the second vector 408b may, for example, correspond to the condition token 132. The distance score 408 may include a measurement the distance between vectors in the word embedding model, as described herein and in the discussion related to FIG. 2.

The medical term linker 128 may further include a prevention repository 410. The prevention repository 410 may include a repository that stores associations between conditions and respective drugs that that prevent the conditions. For example, the prevention repository 410 may store a preventative association 412. The preventative association 412 may include a link between an identifier 414 corresponding to the substance token 130 and an identifier 416 corresponding to the condition token 132. Alternatively or in addition, the preventative association 412 may include information that indicates that the pharmaceutical substance cures, prevents, or otherwise treats the medical condition.

The medical term linker 128 may further include a prevention filter 418. The prevention filter 418 may evaluate whether the pharmaceutical substance corresponding to the substance token 130 treats the medical condition corresponding to the condition token 132. For example, the prevention filter 418 may receive the substance token 130 and the condition token 132. In some examples, the prevention filter 418 may identify respective medical term identifiers corresponding to the substance token 130 and the condition token 132. The prevention filter 418 may search the prevention repository 410 for the preventative association 412 corresponding to the substance token 130 and the condition token 132.

The prevention filter 418 may generate preventative relationship results 420. The preventative relationship results 420 may indicate that the substance corresponding to the substance token 130 cures, prevents, and/or treats the condition corresponding to the condition token 132. The preventative relationship results 420 may include respective medical term identifiers associated with the substance and condition. Alternatively or in addition, the preventative relationship results 420 may include other identifying information stored in the prevention repository 410 and/or the medical term repository related to the substance token 130 and/or the condition token 132.

The medical term linker 128 may include a natural language interpreter 422. The natural language interpreter 422 may identify a causal relationship between character segments in the electronic medical record 102. In other examples, the natural language processor may perform natural language understanding analysis on the electronic medical record or any portion thereof based on a natural language understanding model 424. For example, the medical term linker 128 may include the natural language understanding model 424. The natural language interpreter 422 may determine that the pharmaceutical substance related to the substance token 130 causes the condition related to the condition token 132 by applying the natural language understanding model 424 to the electronic medical record 102, or any portion thereof.

In some examples, the natural language interpreter 422 may compare a portion of the electronic medical record 102 with a keyword. The keyword may include text that indicates causality. For example, they keyword may include "induced" and the natural language interpreter may determine that the text "induced" in the text "Vincristine-induced neuropathic pain" is corresponds to the keyword. In another example, the phrase, "drug A induces condition B on patient", the relation between drug A and condition B is negative based on the keyword 'induce'.

The natural language interpreter 422 may generate the causal relationship results 426. The causal relationship results 426 may include information that indicates whether the pharmaceutical substance related to the substance token 130 causes the condition related to the condition token 132. In addition, the causal relationship results 426 may include identifying information, such as medical identifiers, medical term types, and other information that identifies the pharmaceutical substance and the medical condition. In some examples, the causal relationship results 426 may indicate an existence of a causal relationship between the pharmaceutical substance and the medical condition. In other examples, the causal relationship results 426 may indicate an absence of the causal relationship between the pharmaceutical substance and the medical condition.

The natural language understanding model 424 may include stored information used by the natural language interpreter to identify the causal relationship between the character segments. For example, the natural language understanding model 424 may include rules for dependency parsing to determine the relation between the medical entities in the medical record. In some examples, the natural language understanding model 424 may include a library of instructions, such as for example, spacy, nitk and genism or any other kind of procedural library. Alternatively or in addition, the natural language understanding model 424 may include a dictionary of keywords that define the type of relation between the entities. In some examples, the model may use parts of speech tagger to learn the grammar of the words in the record.

The medical term linker 128 may additionally include the causal detector 428. The causal detector 428 may evaluate the results of one or more models to determine whether the pharmaceutical substance corresponding to the substance token 130 causes the medical condition corresponding to the condition token 132. For example, the causal detector 428 may receive information from one or more sources including the semantic comparator 402, the prevention filter 418 and/or the natural language interpreter 422. The causal detector 428 may perform decision making based on the information to generate the adverse effect information 134.

In some examples, the adverse effect information may include a causal link indication 430. The casual link indication 430 may include an indication that the pharmaceutical substance corresponding to the substance token 130 causes the medical condition corresponding to the condition token 132. Alternatively, the causal link indication 430 may include an indication that a causal link between the substance token 130 and the condition token 132 was not found. The causal link indication 430 may additionally include identifying information related to the substance token 130 and/or the condition token 132. For example, the causal link indication 430 may include the medical term identifier 118, the medical term type 122, the medical term label 120, and any other identifying information described in FIG. 1 or herein.

Figure 5:
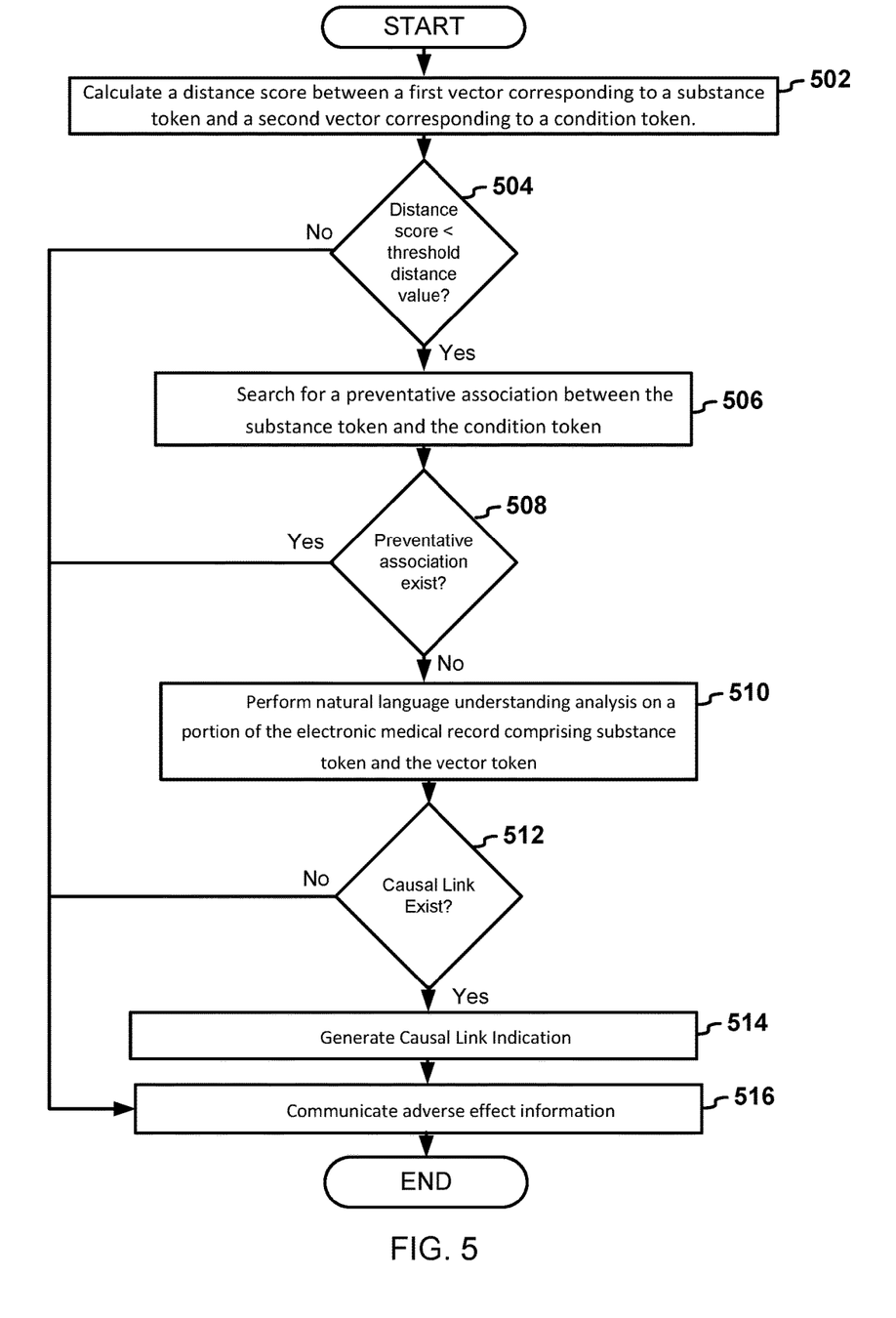
FIG. 5 illustrates an example of flow logic for a medical term linker.

FIG. 5 illustrates an example of flow logic for the medical term linker 128. References to FIG. 4 and FIG. 5 are included in the following discussion of an example of logic implemented by the medical term linker 128.

The semantic comparator 402 may calculate a distance score 408 between the first vector 406a corresponding to the substance token 130 and the second vector 406b corresponding to the condition token 132 (502). The distance score 408 may include a distance between the first vector 406a and the second vector 406b in the word embedding model 110, as described herein. The first vector 406a and the second vector 406b may include examples of the vector 112 illustrated in FIG. 1.

The causal detector 428 may determine whether the distance score 408 is less than a threshold distance value (504). In response to the distance score 408 being greater than the threshold distance value (504, no), the causal detector 428 may communicate the adverse effect association information 134. The adverse effect association information 134 may include an indication that the causal link 130 was not found. In response to the distance score 408 being less than the threshold distance value (504, yes), the prevention filter 418 may search for the preventative association 412 between the substance token 130 and the condition token 132 (506). For example, the prevention filter 418 may search the prevention repository 410 for an association between the substance token 130 and the condition token 132, and/or any identifying information related to the substance token 130 and the condition token 132.

The causal detector 428, may determine whether the preventative association between the substance token 130 and the condition token 132 exists (508). For example, the causal detector 428 may evaluate the preventative relationship results 420 provided by the prevention filter 418. In some examples, the causal relationship results 426 may indicate an absence or an existence of the preventative association 413 between the substance token 130 and the condition token 132.

In response to the existence of the preventative association 413 (508, yes), the causal detector 428 may communicate the adverse effect information 134. For example, the adverse effect information 134 may include an indication that a causal relationship between the substance token 130 and the condition token 132 was not found.

In response to an absence of the preventative association (508, no), the natural language interpreter 422 may perform natural language understanding analysis on a portion of the electronic medical record comprising the substance token 130 and the condition token 132 (510). The natural language interpreter 422 may generate the causal relationship results 426. The causal detector 428 may evaluate the causal relationship results 426 to determine whether the causal link exists between the substance token 130 and the condition token 132 (512).

In response to the existence of the causal link between the substance token 130 and the condition token 132 (512, Yes), the causal detector 428 may generate the causal link indication 430 (514). The causal link indication 430 may include an indication of a causal link between the pharmaceutical substance corresponding to the substance token 130 and the medical condition corresponding to the condition token 132. For example, the causal link indication 430 may include identifying information related to the substance token 130 and the condition token 132, such as the medical term identifier 118, the medical label 120, the medical type 122, the training text, 113 and other identifying information. In addition, the causal link may include a flag that indicates the causal relationship.

The causal detector 428 may communicate adverse effect information 134 (516). The adverse effect information 134 may indicate the existence and/or the absence of the causal link between the substance token 130 and the condition token 132. The adverse effect information 134 may be stored in a memory, such as a database, or communicated over a network. In other example, a display device in communication with the system 100 may display the adverse effect information.

The logic illustrated in the flow diagrams in FIG. 3 and FIG. 5 may include additional, different, or fewer operations than illustrated. For example, the logic illustrated in FIG. 3 may further include the operation of associating the training text 113 corresponding to the context vector with the medical term identifier 118 and/or the medical term label 120 in the medical term repository 116. Alternatively or in addition, the logic illustrated in FIG. 3 may include updating the medical term label 120 in the medical term repository with the training text 113 corresponding to the context vector.

Figure 6:
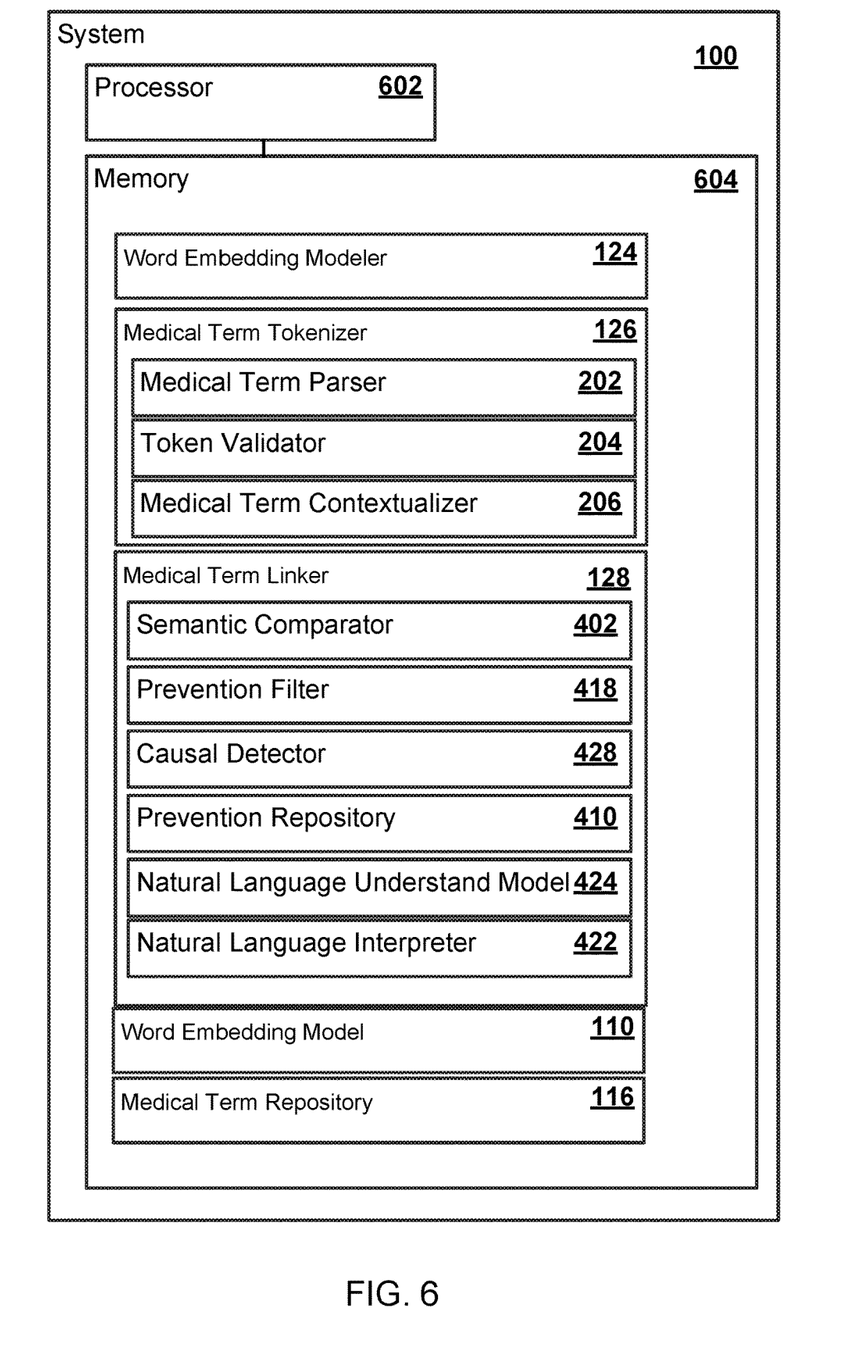
FIG. 6 illustrates an example of a system.

The operations illustrated may be performed in an order different than illustrated. In addition, the system 100 may be implemented with additional, different, or fewer components than illustrated. For example, FIG. 6 illustrates an example of the system 100 that includes a processor 602 and a memory 604.

The processor 602 may be in communication with the memory 604. In one example, the processor 602 may also be in communication with additional elements, such as a network interface (not shown). Examples of the processor 602 may include a general processor, a central processing unit, a microcontroller, a server, an application specific integrated circuit (ASIC), a digital signal processor, a field programmable gate array (FPGA), and/or a digital circuit, analog circuit, or some combination thereof.

The processor 602 may be one or more devices operable to execute logic. The logic may include computer executable instructions or computer code stored in the memory 604 or in other memory that when executed by the processor 602, cause the processor 602 to perform the features implemented by the logic of the word embedding modeler 124, the medical term tokenizer 126, the medical term linker 128 and/or the system 100 or subcomponent in the system 100. The computer code may include instructions executable with the processor 602.

The memory 604 may be any device for storing and retrieving data or any combination thereof. The memory 604 may include non-volatile and/or volatile memory, such as a random access memory (RAM), a read-only memory (ROM), an erasable programmable read-only memory (EPROM), or flash memory. Alternatively or in addition, the memory 604 may include an optical, magnetic (hard-drive) or any other form of data storage device.

The memory 604 may include at least one the word embedding modeler 124, the medical term tokenizer 126, and/or the medical term linker 128. In addition, the memory may include any other component previously discussed, such as word embedding modeler 124, the medical term repository 116, the medical term parser 202, the medical term tokenizer 126, the token validator 204, the medical term contextualizer 206, the medical term linker 128, the semantic comparator 402, the prevention repository 410, the prevention filter 418, the causal detector 428, the natural language interpreter 422, the natural language understanding model 424, and/or other components of the system 100 described herein.

The system 100 may be implemented in many different ways. For example, each component of the system 100 may include a circuit or circuitry. Each circuit or circuitry may be hardware or a combination of hardware and software. The circuitry may include the word embedding modeler 124, the medical term tokenizer 126, and/or the medical term linker 128. In addition, the circuitry may include any other component previously discussed, such as word embedding modeler 124, the medical term repository 116, the medical term parser 202, the medical term tokenizer 126, the token validator 204, the medical term contextualizer 206, the medical term linker 128, the semantic comparator 402, the prevention repository 410, the prevention filter 418, the causal detector 428, the natural language interpreter 422, the natural language understanding model 424, and/or other components of the system 100 described herein. For example, each circuit or circuitry may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each circuitry may include memory hardware, such as a portion of the memory 604, for example, that comprises instructions executable with the processor 602 or other processor to implement one or more of the features of the circuitry. When any one of the circuitry includes the portion of the memory that comprises instructions executable with the processor 602, the circuitry may or may not include the processor 602. In some examples, each circuitry may just be the portion of the memory 604 or other physical memory that comprises instructions executable with the processor 602 or other processor to implement the features of the corresponding circuitry without the circuitry including any other hardware. Because each circuitry includes at least some hardware even when the included hardware comprises software, each circuitry may be interchangeably referred to as a hardware circuitry.

Some features are shown stored in a non-transitory storage medium such as a computer readable storage medium (for example, as logic implemented as computer executable instructions or as data structures in memory). All or part of the system 100 and its logic and data structures may be stored on, distributed across, or read from one or more types of computer readable storage media. Examples of the non-transitory computer readable storage medium may include a hard disk, a floppy disk, a CD-ROM, a flash drive, a cache, volatile memory, non-volatile memory, RAM, flash memory, or any other type of computer readable storage medium or storage media. The non-transitory computer readable storage medium may include any type of non-transitory computer readable medium, such as a CD-ROM, a volatile memory, a non-volatile memory, ROM, RAM, or any other suitable storage device.

The processing capability of the system 100 may be distributed among multiple entities, such as among multiple processors and memories, optionally including multiple distributed processing systems. Parameters, databases, and other data structures may be separately stored and managed, may be incorporated into a single memory or database, may be logically and physically organized in many different ways, and may implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL)).

All of the discussion, regardless of the particular implementation described, is illustrative in nature, rather than limiting. For example, although selected aspects, features, or components of the implementations are depicted as being stored in memory(s), all or part of the system 100 or systems may be stored on, distributed across, or read from other computer readable storage media, for example, secondary storage devices such as hard disks, flash memory drives, floppy disks, and CD-ROMs. Moreover, the various modules, circuitry and screen display functionality is but one example of such functionality and any other configurations encompassing similar functionality are possible.

The respective logic, software or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one example, the instructions are stored on a removable media device for reading by local or remote systems. In other examples, the logic or instructions are stored in a remote location for transfer through a computer network or over telephone lines. In yet other examples, the logic or instructions are stored within a given computer, central processing unit ("CPU"), graphics processing unit ("GPU"), or system.

Furthermore, although specific components are described above, methods, systems, and articles of manufacture described herein may include additional, fewer, or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same apparatus executing a same program or different programs. The components may be resident on separate hardware, such as separate removable circuit boards, or share common hardware, such as a same memory and processor for implementing instructions from the memory. Programs may be parts of a single program, separate programs, or distributed across several memories and processors.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations.

The subject-matter of the disclosure may also relate, among others, to the following aspects:

1. A system comprising:
    a processor;
    a medical term tokenizer executable by the processor to tokenize an electronic medical record for a plurality of tokens, the plurality of tokens including a substance token corresponding to a pharmaceutical substance identified in the electronic medical record and a condition token corresponding to a medical condition identified in the electronic medical record;
    a semantic comparator executable by the processor to generate a distance score between a first vector of a word embedding model and a second vector of the word embedding model, the first vector corresponding to the substance token and the second vector corresponding to the condition token;
    a medical term contextualizer executable by the processor to detect an absence of a preventative association between the substance token and the condition token in a prevention repository configured to link a first medical term corresponding to the pharmaceutical substance with a second medical term corresponding to the medical condition; and
    a token validator executable by the processor to generate a causal link indication indicative of a causal link between the substance token and the condition token in response to the distance score being greater than a threshold value and in response to detection of the absence of the preventative association between the substance token and the condition token.

2. The system of aspect 1, further comprising
    a natural language interpreter executable by the processor to perform natural language understanding of a portion of the electronic medical record in response to the distance score being greater than a threshold value and in response to the absence of the preventative association between the substance token and the condition token, the portion of the electronic medical record comprising text corresponding to the substance token and the condition token.

3. The system of any of aspects 1 to 2, wherein the natural language interpreter is further executable by the processor to identify a keyword in the portion of the electronic medical record, the keyword stored in association with a natural language understanding model.

4. The system of any of aspects 1 to 3, wherein the medical term tokenizer is configured to authenticate that a medical term is representative of a character segment of the electronic medical record based on a comparison of the character segment with a medical term label associated with the medical term, wherein the medical term label is different from the character segment.

5. The system of any of aspects 1 to 4, wherein the medical term tokenizer further comprises:
    a medical term parser executable by the processor to identify a character segment in the electronic medical record, the medical term parser further executable by the processor to generate, based on a comparison of the character segment with a medical term label, a first confidence score that the medical term label represents the character segment;
    a medical term contextualizer executable by the processor to generate a context comprising text adjacent to the character segment in the electronic medical record, the medical term contextualizer further executable by the processor to calculate a second confidence score, the second confidence score including a probability that a target vector is associated with a context vector in the word embedding model, the context vector corresponding to the context and the target vector corresponding to training text stored in association with the word embedding model; and
    a token validator executable by the processor to generate at least one of the tokens, the at least one of the tokens associated with the training text in response to the second confidence score being greater than a second threshold value.

6. The system of any of aspects 1 to 5, wherein the medical term contextualizer is further executable by the processor to calculate a distance between the target vector and the context vector, wherein the second confidence score is based on the distance between the target vector and the context vector.

7. The system of any of aspects 1 to 6, wherein the word embedding model comprises a word2vec model.

8. A computer-implemented method, comprising:
tokenizing an electronic medical record for a plurality of tokens, the plurality of tokens including a substance token corresponding to a pharmaceutical substance and a condition token corresponding to a medical condition;
generating a distance score between a first vector of a word embedding model and a second vector of the word embedding model, the first vector corresponding to the substance token and the second vector corresponding to the condition token;
detecting an absence of a preventative association between the substance token and the condition token in a prevention repository configured to link a first medical term corresponding to the pharmaceutical substance with a second medical term corresponding to the medical condition; and
communicating in response to the absence of the preventative association and the distance score being less than a threshold value, adverse effect information, the adverse effect information including a causal link indication comprising the first medical term and the second medical term.

9. The computer-implemented method of aspect 8, further comprising:
performing in response to the absence of the preventative association and the distance score being less than a threshold value, natural language understanding analysis on a portion of the electronic medical record comprising the substance token and the condition token, the natural language understanding analysis identifying a causal link between the substance token and the condition token.

10. The computer-implemented method of any of aspects 8 to 9, further comprising
authenticating that at least one of the first medical term and the second medical term is representative of a character segment of the electronic medical record based on a comparison of the character segment with a medical term label, wherein the medical term label is different from the character segment 11. The computer-implemented method of any of aspects 8 to 10, wherein tokenizing the electronic medical record further comprises:
Parsing the electronic medical record for a character segment;
determining, based on a comparison of the character segment with a medical term label, a first confidence score that the medical term label represents the character segment;
parsing in response to the first confidence score being less than a first threshold value, the electronic medical record for a context of the character segment, the context comprising text adjacent to the character segment in the electronic medical record;
determining a second confidence score including a probability that a target vector is associated with a context vector in the word embedding model, the context vector corresponding to the context and the target vector corresponding to training text stored in the word embedding model; and
generating in response to the second confidence score being greater than second threshold value, at least one of the tokens, the at least one of the tokens associated with the training text.

12. The computer-implemented method of any of aspects 8 to 11, wherein the second confidence score is based on a distance between the target vector and the context vector in the word embedding model.

13. The computer-implement method of any of aspects 8 to 12, wherein the distance score comprises an angular distance measurement.

14. The computer-implement method of any of aspects 8 to 13, further comprising associating the training text with the medical term label in a medical term repository, wherein the medical term label comprises text that is different from the training text.

15. A non-transitory storage medium comprising computer executable instructions, the computer executable instructions executable by a processor in communication with the non-transitory storage medium, the computer executable instructions comprising:
instructions executable by the processor to tokenize an electronic medical record for a plurality of tokens, the plurality of tokens including a substance token corresponding to a pharmaceutical substance and a condition token corresponding to a medical condition;
instructions executable by the processor to calculate a distance score between a first vector of a word embedding model and a second vector of the word embedding model, the first vector corresponding to the substance token and the second vector corresponding to the condition token;
instructions executable by the processor to search for a preventative association between the substance token and the condition token in a prevention repository configured to link a first medical of the pharmaceutical substance with a second medical of the medical condition; and
instructions executable by the processor to communicate adverse effect association information indicative of a causal link between the substance token and the condition token.

16. The non-transitory storage medium of aspect 15, further comprising:
instructions executable by the processor to perform, in response to an absence of the preventative association and the distance score being less than a threshold value, natural language understanding analysis on a portion of the electronic medical record to the causal link between the substance token and the condition token.

17. The non-transitory storage medium of any of aspects 15 to 16, further comprising
instructions executable by the processor to identify a character segment;
instructions executable by the processor to generate, based on a comparison of the character segment with a medical term label, a first confidence score that the medical term label represents the character segment;
instructions executable by the processor to parse the electronic medical record for a context of the character segment in response to the first confidence score being less than a first threshold value, the context comprising text adjacent to the character segment in the electronic medical record;
instructions executable by the processor to generate a second confidence score, the second confidence score including a probability that a target vector is associated with a context vector in the word embedding model, the second confidence score based on a distance between the target vector and the context vector in the word embedding model, the context vector corresponding to the context and the target vector corresponding to training text stored in the word embedding model; and instructions executable by the processor generate at least one of the tokens, the at least one of the tokens associated with the training text in response to the second confidence score being greater than second threshold value.

18. The non-transitory storage medium of any of aspects 15 to 18, wherein the word embedding model comprises a continuous bag of words neural network.

19. The non-transitory storage medium of any of aspects 15 to 18, further comprising:

instructions executable by the processor to verify that a medical term is representative of a character segment of the electronic medical record based on a comparison of the character segment with a medical term label associated with the medical term in a medical term repository, wherein the medical term label is different from the character segment.

20. The non-transitory storage medium of any of aspects 15 to 19, wherein the distance score is based on a cosine similarity score or a cosine distance score.

What is claimed is:

1. A system comprising:
a processor;
a medical term tokenizer executable by the processor to:
tokenize an electronic medical record into a plurality of tokens, the plurality of tokens including a substance token corresponding to a pharmaceutical substance identified in the electronic medical record and a condition token corresponding to a medical condition identified in the electronic medical record, and
parse the electronic medical record for a context of the condition token, the context comprising at least one of the tokens that are adjacent to the condition token in the electronic medical record;
a medical term contextualizer executable by the processor to:
determine a first vector of a word embedding model based on the substance token, the word embedding model comprising a plurality of vectors representative of training tokens derived from a plurality of medical records, and
determine, based on a continuous bag of words neural network model, a second vector of the word embedding model, the second vector representative of an alternative token, the alternative token being different from the condition token;
a semantic comparator executable by the processor to generate, based on a skip gram neural network model, a distance score between the first vector of the word embedding model and the second vector of the word embedding model;
a medical term contextualizer executable by the processor to detect, in response to the distance score being less than a threshold value, an absence of a preventative association between the substance token and the alternative token in a prevention repository, the prevention repository configured to link a first medical term corresponding to the pharmaceutical substance with a second medical term corresponding to the medical condition; and
a token validator executable by the processor to generate a causal link indication indicative of a causal link between the pharmaceutical substance and the medical condition in response to the distance score being greater than a threshold value and in response to detection of the absence of the preventative association between the substance token and the condition token.

2. The system of claim 1, further comprising
a natural language interpreter executable by the processor to perform natural language understanding of a portion of the electronic medical record in response to the distance score being greater than a threshold value and in response to the absence of the preventative association between the substance token and the alternative token, the portion of the electronic medical record comprising text corresponding to the substance token and the condition token.

3. The system of claim 2, wherein the natural language interpreter is further executable by the processor to identify a keyword in the portion of the electronic medical record, the keyword stored in association with a natural language understanding model.

4. The system of claim 1, wherein the medical term tokenizer further comprises:
a medical term parser is further executable by the processor to:
identify a character segment in the electronic medical record, the character segment corresponding to the condition token;
generate, based on a comparison of the character segment with a medical term label for the medical condition, a first confidence score that the medical term label represents the medical condition;
calculate, in response to the first confidence score being less than a first confidence threshold, a second confidence score, the second confidence score including a probability that the second vector is associated with a context vector in the word embedding model, the context vector corresponding to the context and the second vector corresponding to training text stored in association with the word embedding model; and
identify, in the word embedding model and in response to the second confidence score being less than a second confidence threshold, the alternative token corresponding to the second vector.

5. The system of claim 4, wherein the medical term contextualizer is further executable by the processor to calculate a distance between the second vector and the context vector, wherein the second confidence score is based on the distance between the second vector and the context vector.

6. The system of claim 4, further comprising a memory configured to store a plurality of word2vec models, the word2vec models comprising the word embedding model, the continuous bag of words neural network model, and the skip gram neural network model.

7. A computer-implemented method, comprising:
tokenizing an electronic medical record for a plurality of tokens, the plurality of tokens including a substance token corresponding to a pharmaceutical substance and a condition token corresponding to a medical condition;
identifying a first vector of a word embedding model based on the substance token, the word embedding model comprising a plurality of vectors previously determined based a plurality training tokens derived from medical records;

parsing the electronic medical record for a context of the condition token, the context comprising at least one of the tokens adjacent to the condition token in the electronic medical record;
determining, based the context and a continuous bag of words neural network model, a second vector representative of an alternative token included in the training tokens, the alternative token different from the condition token and representative of the medical condition;
generating a distance score between the first vector of the word embedding model and the second vector of the word embedding model;
detecting, in response to the distance score being less than a threshold value, an absence of a preventative association between the substance token and the alternative token in a prevention repository, the preventive repository configured to link a first medical term corresponding to the pharmaceutical substance with a second medical term corresponding to the medical condition; and
communicating, in response to the absence of the preventative association and the distance score being less than a threshold value, adverse effect information, the adverse effect information including a causal link indication comprising the first medical term and the second medical term.

8. The computer-implemented method of claim 7, further comprising:
performing in response to the absence of the preventative association and the distance score being less than a threshold value, natural language understanding analysis on a portion of the electronic medical record comprising the substance token and the condition token, the natural language understanding analysis identifying a causal relationship between the substance token and the alternative token.

9. The computer-implemented method of claim 7, wherein determining, based on the context, the second vector of the word embedding model further comprises:
determining a confidence score including a probability that the second vector is associated with a context vector in the word embedding model, the context vector corresponding to the context; and
selecting in response to the confidence score being greater than a threshold value, the second vector from the plurality of vectors.

10. The computer-implemented method of claim 9, wherein the confidence score is based on a distance between the second vector and the context vector in the word embedding model.

11. The computer-implement method of claim 7, wherein the distance score comprises an angular distance measurement.

12. The computer-implement method of claim 7, further comprising
determine that a character segment of the alternative token is not included in a medical term repository; and
associating the character segment of the alternative token with a medical term label in a medical term repository.

13. A non-transitory storage medium comprising computer executable instructions, the computer executable instructions executable by a processor in communication with the non-transitory storage medium, the computer executable instructions comprising:
instructions executable by the processor to tokenize an electronic medical record for a plurality of tokens, the plurality of tokens including a substance token corresponding to a pharmaceutical substance and a condition token corresponding to a medical condition;
instructions executable by the processor to determine a first vector of a word embedding model, the first vector representative of the condition token, the word embedding model comprising vectors representative of training tokens, the training tokens including the condition token;
instructions executable by the processor to parse the electronic medical record for a context of the substance token, the context comprising at least one of the tokens adjacent to the substance token in the electronic medical record;
instructions executable by the processor to determine, based on the context and a continuous bag of words neural network model, a second vector of the word embedding model, the second vector representative of an alternative token included in the training tokens, the alternative token representative of the pharmaceutical substance and comprising text different from the text of the substance token;
instructions executable by the processor to calculate, based on a skip-gram neural network model, a distance score between the first vector of a word embedding model and the second vector of the word embedding model;
instructions executable by the processor to search, in response to the distance score being less than a threshold value, for a preventative association between the alternative token and the condition token in a prevention repository, the prevention repository configured to link a first medical of the pharmaceutical substance with a second medical of the medical condition; and
instructions executable by the processor to communicate adverse effect association information indicative of a causal link between the pharmaceutical substance and the medical condition.

14. The non-transitory storage medium of claim 13, further comprising:
instructions executable by the processor to perform, in response to an absence of the preventative association and the distance score being less than a threshold value, natural language understanding analysis on a portion of the electronic medical record that includes the substance token and the condition token and generate natural language text and determine, based on the natural language understanding analysis, the causal link between the pharmaceutical substance and the medical condition.

15. The non-transitory storage medium of claim 13, further comprising
instructions executable by the processor to identify a character segment in the substance token;
instructions executable by the processor to generate, based on a comparison of the character segment with a medical term label associated with the medical substance, a first confidence score that the character segment represents the medical substance;
instructions executable by the processor to generate a second confidence score, the second confidence score including a probability that the second vector is associated with a context vector in the word embedding model, the second confidence score based on a distance between the second vector and the context vector in the word embedding model, the context vector corresponding to training text stored in the word embedding model that matches the context; and instructions executable by the processor receive the alternative token from the word embedding model in response to the second confidence score being greater than a second threshold value.

16. The non-transitory storage medium of claim 13, further comprising:
instructions executable by the processor to verify that a medical term is representative of a character segment of the electronic medical record based on a comparison of the character segment with a medical term label associated with the medical term in a medical term repository, wherein the medical term label is different from the character segment.

17. The non-transitory storage medium of claim 13, wherein the distance score is based on a cosine similarity score or a cosine distance score.

* * * * *